(12) United States Patent
Lair

(10) Patent No.: US 11,007,123 B2
(45) Date of Patent: *May 18, 2021

(54) ENTERAL SAFETY SYSTEM AND METHODS

(71) Applicant: NeoMed, Inc., Woodstock, GA (US)

(72) Inventor: Anthony C. Lair, Alpharetta, GA (US)

(73) Assignee: NeoMed, Inc., Woodstock, GA (US)

( * ) Notice: Subject to any disclaimer, the term of this patent is extended or adjusted under 35 U.S.C. 154(b) by 99 days.

This patent is subject to a terminal disclaimer.

(21) Appl. No.: 16/279,461

(22) Filed: Feb. 19, 2019

(65) Prior Publication Data

US 2019/0254932 A1     Aug. 22, 2019

Related U.S. Application Data

(63) Continuation of application No. 13/873,090, filed on Apr. 29, 2013, now Pat. No. 10,245,217, which is a (Continued)

(51) Int. Cl.
*A61J 15/00* (2006.01)
*A61M 39/10* (2006.01)

(52) U.S. Cl.
CPC .......... *A61J 15/0003* (2013.01); *A61J 15/00* (2013.01); *A61J 2200/76* (2013.01); (Continued)

(58) Field of Classification Search
CPC .... A61J 15/00; A61J 15/0003; A61J 2200/76; A61J 2205/20; A61M 2202/0482; A61M 2205/6081; A61M 39/10
See application file for complete search history.

(56) References Cited

U.S. PATENT DOCUMENTS 4,180,076 A   12/1979  Betancourt
4,390,017 A    6/1983  Harrison et al.
(Continued)

OTHER PUBLICATIONS

Utah Medical Products Inc., www.utahmed.com/nutricath.htm, Jan. 5, 2008, 5 pgs.
(Continued)

*Primary Examiner* — Brandy S Lee
(74) *Attorney, Agent, or Firm* — Dority & Manning, P.A.

(57) ABSTRACT

Enteral safety system (ESS) may include syringe having visual indicator such as barrel with measurement marks of a color. Barrel may allow content viewing. ESS may include hub for connecting syringe to enteral set. Hub may have a visual indicator such as being same color as barrel's marks. Enteral tubing or set may have a visual indicator such as a lengthwise stripe same color as barrel's marks. Enteral tubing may allow content viewing. ESS may include an enteral tubing-feeding tube hub for connecting enteral tubing to a feeding tube. This hub may have visual indicator such as same color as barrel's marks. Feeding tube may have visual indicator such as a lengthwise stripe same color as barrel's marks. Feeding tube may allow content viewing. The syringe, syringe-enteral tubing hub, enteral tubing, enteral tubing-feeding tube hub, and feeding tubing are properly connectable by reference to visual indicators such as color matching.

2 Claims, 3 Drawing Sheets

Related U.S. Application Data continuation of application No. 11/935,510, filed on Nov. 6, 2007, now Pat. No. 8,430,865.

(60) Provisional application No. 60/884,408, filed on Jan. 10, 2007.

(52) U.S. Cl.
CPC .......... *A61J 2205/20* (2013.01); *A61M 39/10* (2013.01); *A61M 2202/0482* (2013.01); *A61M 2205/6081* (2013.01)

(56) References Cited

U.S. PATENT DOCUMENTS

| | | | |
|---|---|---|---|
| 4,781,704 | A | 11/1988 | Potter |
| 5,267,983 | A | 12/1993 | Oilschlager et al. |
| 6,482,170 | B1 | 11/2002 | Andersen |
| 6,613,012 | B2 * | 9/2003 | Kraushaar ............... A61M 5/14 40/630 |
| 7,024,088 | B1 | 4/2006 | Davis |
| 7,195,612 | B2 | 3/2007 | Van Sloten et al. |
| 8,430,865 | B2 | 4/2013 | Lair |
| 10,245,217 | B2 * | 4/2019 | Lair .................... A61J 15/0003 |
| 2007/0060898 | A1 | 3/2007 | Shaughnessy et al. |
| 2007/0112323 | A1 * | 5/2007 | Daly ..................... A61M 39/08 604/411 |

OTHER PUBLICATIONS

Welcome to neoDevices, www.neodevices.com/html/about/html, Jan. 5, 2008, 4 pgs.
Peggi Guenter et al., Enteral Feeding Misconnections: A Consortium Position Statement, The Joint Commission, Journal on Quality and Patient Safety, May 2008, vol. 34 No. 5, pp. 285-292, 8 pgs.
RxZone.us, Enteral feeding syringe, www.rxzone.us, 2 pgs.
Nutrisafe2, www.oxygenusa.com, 3 pgs.
David Copelan et al., Implementation of an Enteral Nutrition and Medication Administration System Utilizing Oral Syringes in the NICU, Neonatal Network, vol. 25, No. 1, Jan./Feb. 2006, 4 pgs.
NeoDevices Inc., Enteral Extension Sets, www.neodevices.com, 2 pgs.
Enteral Feeding Set Adapters and Connectors, Association for the Advancement of Medical Instrumentation, ANSI/AAMIM ID54:1996/(R)2005, 7 pgs.
Tubing Misconnections—Persistent and Potentially Deadly Occurrence, Sentinel Event Alert from the Joint Commission Website: www.jointcommission.org, Issue 36, Apr. 3, 2006, 4 pgs.
ISMP Medication Safety Alert!, Jun. 15, 1006, vol. 11, Issue 12, 2 pgs.
A Spectrum of Problems with Using Color, ISMP Medication Safety Alert!, Jun. 15, 2006, vol. 11, Issue 12, 2 pgs.
Tracheal Cuff Inflation Tube Mistaken for Enteral Feeding Tube, ECRI Institute's Medical Device Safety Reports, Health Devices, Feb.-Mar. 1985;15(2-3):64-5, www.mdsr.ecri.org, 2 pgs.
About the Color Coding Kids Hospital System, Vital-Signs Inc. 2007, www.colorcodingkids.com, 1 pg.
Peggi Guenter et al., Enteral Feeding Misconnections: An Update, Nutrition in Clinical Practice, 2009, 24, 325, http://ncp.sagepub.com, 11 pgs.

* cited by examiner

ENTERAL SAFETY SYSTEM AND METHODS

CROSS-REFERENCE TO RELATED APPLICATION

The present application claims priority to and benefit of the prior filed and commonly owned provisional application, filed in the United States Patent and Trademark Office on Jan. 10, 2007, assigned Ser. No. 60/884,408, entitled Enteral Safety System and Methods, and incorporated herein by reference.

FIELD OF THE INVENTIONS

The inventions relate generally to medical devices and methods, and particularly relate to enteral safety systems and methods relating thereto.

BACKGROUND

Enteral feeding systems are generally described in the patent to Anderson, U.S. Pat. No. 6,482,170, incorporated herein by reference, and entitled: Apparatus and Method for Relieving Gastric Pressure During Enteral Feeding.

With respect to enteral feeding systems, errors in tubing and catheter mis-connection have led to such tragedies as patient deaths and permanent loss of function. Several factors contribute to tubing errors. A first factor is the similarity in appearance of tubes, catheter connections, and other medical components and accessories that have dissimilar functions. Another factor is the prevalent use of luer connectors that enable functionally dissimilar tubes or catheters to be connected. Yet another factor contributing to errors in tubing and catheter connection is the positioning of functionally dissimilar tubes used in close proximity to one another in patient care. Other factors include the use of tubes or catheters for unintended purposes, movement of patients from one setting or service to others, and staff fatigue.

The factors presented above and others are further delineated in the article entitled *Tubing Misconnections—a Persistent and Potentially Deadly Occurrence* presented as a Sentinel Event ALERT in Issue 36—Apr. 3, 2006 from the Joint Commission Website: www.jointcommission.org. The article is incorporated herein by reference and is attached with this filing.

SUMMARY

Generally stated, the inventions relate to enteral safety systems and methods. The inventions are described herein as being used with specific elements and features, but should not be limited to the particular examples given. One or more of the inventions may be used in other circumstances and/or with other elements or features.

An enteral safety system (ESS) may use several types of elements including an oral dispenser, a hub connecting the oral dispenser to enteral tubing, and another hub connecting the enteral tubing to a feeding tube. Other elements may be included or substituted and the principles of the inventions may be applied thereto.

A first exemplary embodiment of the inventions is an enteral safety system including an oral dispenser with a barrel. An oral dispenser may be referred to herein as a dispenser, an oral syringe, and/or a syringe. Colored measurement marks are included on the barrel. The barrel may allow viewing of barrel content such as by being at least partially transparent. The oral dispenser is connected by a oral dispenser-enteral tubing hub to enteral tubing. The entire oral dispenser-enteral tubing hub is the same color as the measurement marks on the barrel of the oral dispenser. Alternatively, only part of the hub may be the same color as the measurement marks.

In this first exemplary embodiment, the enteral tubing includes a lengthwise stripe the color of the measurement marks on the barrel of the oral dispenser. The lengthwise stripe is continuous and runs the entire length of the tubing, but it could be dashed, run only part of the length of the tubing, etc. The enteral tubing may allow for viewing its contents by being at least partially transparent.

An enteral tubing-feeding tube hub connects the enteral tubing to a feeding tube. The entire enteral tubing-feeding tube hub is the same color as the measurement marks on the barrel of the oral dispenser. Alternatively, only part of the hub may be the same color as the measurement marks.

The feeding tube has a lengthwise stripe the color of the measurement marks on the barrel of the oral dispenser. In this embodiment, the lengthwise stripe is continuous and runs the entire length of the tubing, but it could be dashed, run only part of the length of the tubing, etc. The feeding tube may allow viewing of tube content by being at least partially transparent. Advantageously, this first exemplary ESS provides for proper connection of its elements by color matching.

A second exemplary embodiment according to the inventions provides an ESS that uses a matching feature(s) for proper connection of elements. This exemplary ESS includes an oral dispenser having a matching feature, and a oral dispenser-enteral tubing hub for connecting the oral dispenser to enteral tubing. The hub and the enteral tubing each include the matching feature. The second exemplary ESS also includes an enteral tubing-feeding tube hub for connecting the enteral tubing to a feeding tube. This hub and the feeding tube each include the matching feature. Advantageously, the elements of this second exemplary ESS are properly connectable by reference to the matching features.

Color may be used as a matching feature in the second exemplary ESS. The measurement marks on the barrel of the oral dispenser may be the color chosen as the matching feature. The barrel may allow viewing of barrel content and may be at least partially transparent. The oral dispenser-enteral tubing hub may be the color selected as the matching feature, in whole or in part. The enteral tubing may include the matching feature by a stripe of the chosen color that may run the entire or part of length of the tubing (continuously, in dashes, or otherwise). The enteral tubing may allow viewing of its content. The enteral tubing-feeding tube hub may be the color selected as the matching feature, in whole or in part. The feeding tube may include the matching feature by a stripe of the chosen color that may run the entire or part of the length of the tubing (continuously, in dashes, or otherwise). The feeding tube may allow viewing of its content.

A matching feature as used in the second embodiment may be something other than color, or color in combination with something else. A matching feature may be identical from element to element, or may vary from element to element, or may vary in some cases and not in others.

A third exemplary embodiment according to the inventions provides a method for creating an ESS. By this method, the following elements are provided: a oral dispenser, a first hub for connecting the oral dispenser to enteral tubing, and a second hub for connecting the enteral tubing to a feeding tube. All of these elements are made respectively to include a visual indicator such as a particular color, graphic image, text, or combination thereof. The exemplary method creates the ESS by connecting the elements with reference to each visual indicator.

A fourth exemplary embodiment according to the inventions provides an ESS with elements including a oral dispenser, a first hub for connecting the syringe to enteral tubing, and a second hub for connecting the enteral tubing to a feeding tube. A matching feature is displayed respectively on each of the elements. Advantageously, the matching feature is used to facilitate connection of only the elements displaying the matching feature into the exemplary ESS.

In this fourth embodiment, the matching element may be substantially the same on each element, or the matching element may vary from element to element of the elements of the enteral safety system. For example, the oral dispenser may include a matching feature in the form of an orange letter "S"; the first hub may include a matching feature in the form of an orange letter "H"; the enteral tubing may include a matching feature in the form of an orange stripe the length of the tubing; the second hub may include a matching feature in the form of an orange letter "H"; and the feeding tube may include a matching feature in the form of a dashed orange stripe disposed along part of the length of the tubing.

Four exemplary embodiments according to the inventions have been summarized above. Many more are possible; the inventions are not to be limited to these examples. Other features and advantages of the inventions may be more clearly understood and appreciated from a review of the following detailed description and by reference to the appended drawings and claims.

DETAILED DESCRIPTION

The inventions are described herein with reference to exemplary embodiments, alternative embodiments, and also with reference to the attached drawings. The inventions, however, can be embodied in many different forms and carried out in a variety of ways, and should not be construed as limited to the embodiments set forth in this description and/or the drawings. The exemplary embodiments that are described and shown herein are only some of the ways to implement the inventions. Elements and/or actions of the inventions may be assembled, connected, configured, and/or taken in an order different in whole or in part from the descriptions herein.

Generally stated, the inventions relate to medical devices that eliminate or at least reduce the factors and circumstances that lead to errors in tubing and catheter connection. The inventions include systems and methods having easily matched system elements. Advantageously, these system elements also may be made so that they generally cannot be used with other systems. The exemplary elements cannot be used generally with other systems and devices because the inventions' connectors (also referred to as "hubs") cannot be used generally with such other systems and devices. Thus, the elements of a system may be properly connected based on matching elements, and mismatches may be precluded if the incompatibility feature is also included in the system.

In the exemplary system, elements are easily matched based on a common color or color scheme (or other matching feature) used in such elements. The exemplary system elements also may incorporate transparency or at least partial transparency for ease of use and for ready viewing of the contents of the matched elements.

An exemplary embodiment of the inventions includes a system having variously sized system elements that may include oral dispensers, extension sets, enteral tubes, feeding tubes, and/or hubs (or other connectors) and/or other elements. The system elements may be made of any appropriate elements such silicone, polyurethane, or otherwise. The elements of a system may be easily determined by a matching feature(s) common to the elements of the system. A matching feature also may be referred to as a matchable feature or a visual indicator. Advantageously, the inventions overcome the drawbacks of the prior art by providing systems and methods having elements that match by having a matching feature so that errors in connection cannot be made (or at least are minimized) when only matching elements are connected.

An exemplary embodiment of the inventions uses color as a matching feature common to elements of a particular system or method according to the inventions. The color, however, may be used as a matching feature together with transparency of the elements so as to facilitate viewing the contents of the elements. Instead of color, a matching feature may be a graphic image, text, and/or a combination of color, graphic image, and/or text.

Figure 1:
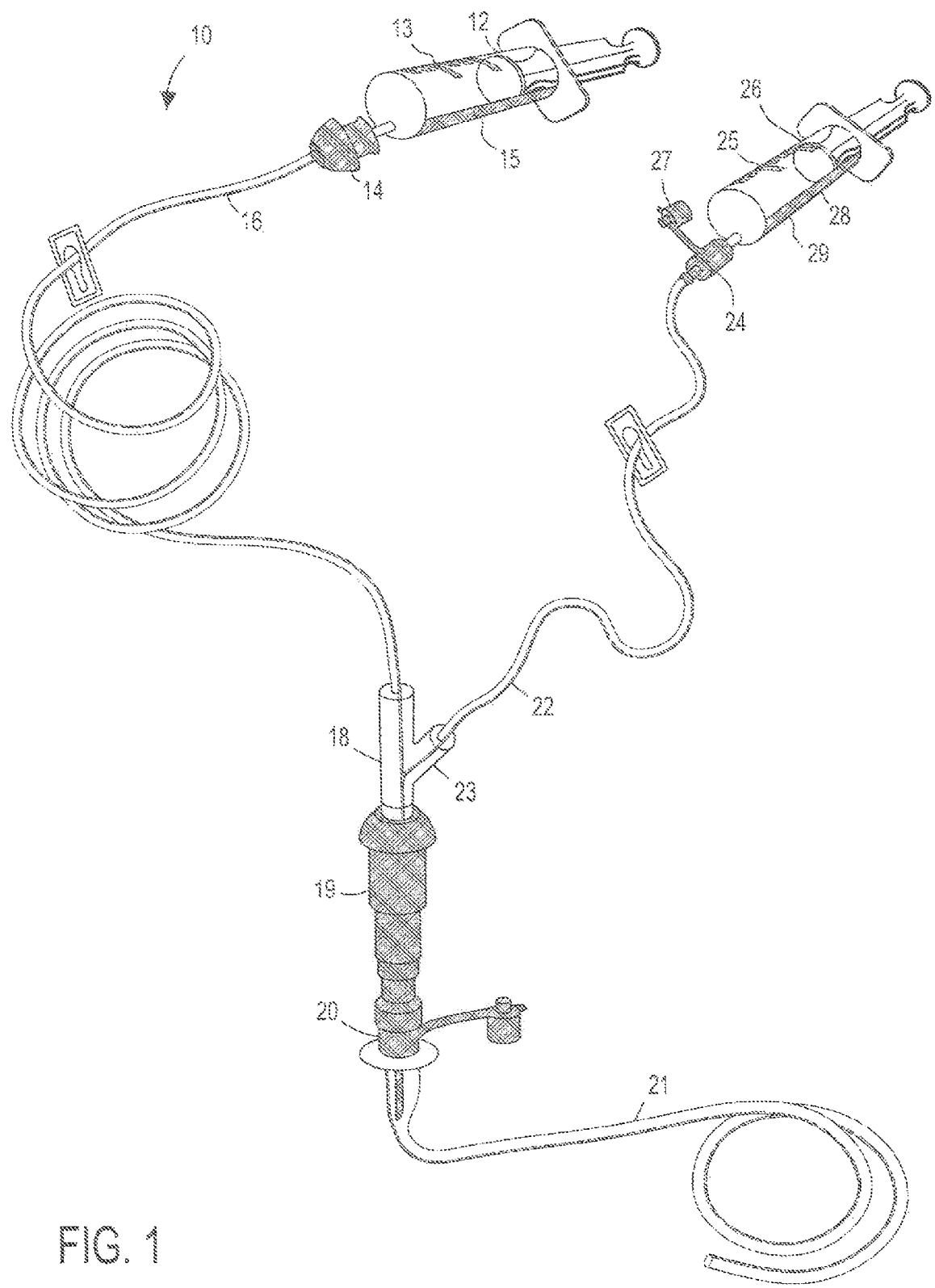
FIG. 1 shows an exemplary embodiment according to the inventions.

FIG. 1 illustrates an exemplary embodiment of an enteral safety system 10 using a particular shade of orange (Pantone 021) as a matching feature among the system elements. In particular, the system elements of the exemplary enteral safety system 10 include a oral dispenser 12 connected at its tip to a hub 14, which, in turn, is connected to an extension set (also referred to as enteral tubing) 16. A side port element 18 connects the extension set 16 via an oral tip 19 to a hub 20 that connects to a feeding tube 21. The side port element 18 also connects another extension set 22 (also referred to as enteral tubing 22) via the oral tip 19 and hub 20 to the feeding tube 21. At its end opposite the side port element 18, the second extension set 22 is connected in series to a hub 24 and then to a oral dispenser 26. The hub 24 includes a tethered plug 27.

In the exemplary embodiment 10, the matching feature is the color orange. Each of the elements of the enteral safety system 10 is orange, is transparent except for a part being orange in color, or has orange as a matching feature otherwise. By using color as a matching feature, a user can easily make connections among the system elements having the matching feature and be assured of proper connections. Another embodiment of the inventions may include one or more elements in an enteral safety system that do not include the matching feature. The matching feature may be omitted from elements that are not disconnectable as provided, and/or are not used as part of the connection process of the enteral safety system. Thus, the use of matching features on elements of an enteral safety system should not be limited to those elements presented herein, but the matching feature may be used on other elements (or may be omitted from elements) such as may be used with an enteral safety system, even if not herein included in the description.

The oral dispensers 12, 26 of the enteral safety system 10 include barrels that are substantially transparent, but use the color orange for all of the markings on the syringes 13, 15 and 25, 29. Thus, the measurement marks 13, 25 on the oral dispensers 12, 26 are orange as well as the graphics and texts 15, 29 for the trademark, place and identity of manufacture. The graphics and texts 15, 29 are represented by orange stripes on the respective oral dispensers 12, 26. An advantage of this exemplary embodiment is that the remainders of the barrels of the oral dispensers are relatively clear or transparent. A user may view the contents of the oral dispensers as well as being able to readily distinguish the matching feature of the color orange as used on the oral dispensers. An alternative embodiment may provide one or more oral dispensers which are only partially transparent, and/or allow viewing of content in another manner.

On the exemplary oral dispenser s 12, 26 described immediately above, all of the markings 13, 15 and 25, 29 on the syringes are of the same color orange to constitute the matching feature according to the inventions. A matching feature, however, in other syringe embodiments may be constituted in other ways. For example, only the measurement markings may be made a specific color (such as orange) and such orange measurement markings may constitute the matching feature. As another example, a graphic element and/or text may be used on the syringe as the feature to be matched to other elements (in color and/or some other feature). These graphic elements or text may have their own design in common, and/or may have color in common. Another embodiment may include one or more syringes that have the matching feature in a different configuration. For example, a syringe may have only one or more of its measurement marks or markings in the color that is used as the matching feature. The other information and/or graphics on the syringe may be any other color. Alternatively, a syringe may include a matching feature that is separate from the measurement markings and/or other information or graphics on the syringe. As an example, a syringe may include a letter "S" (for syringe, but other letters may be used) of a certain color, font, and/or size for use as a matching feature. These alternative implementations of a matching feature apply to the other elements of the exemplary enteral safety system 10.

Referring again to FIG. 1, the exemplary syringes 12, 26 are connected at their respective tips, respectively, to hubs 14, 24, which may also be referred to as syringe-enteral tubing hubs to distinguish them from other hubs. In this example, both hubs 14, 24 are completely of the same color orange as used as the matching feature on the syringes 12, 26. The common matching feature of the particular color orange allows a user to accurately connect a syringe according to the inventions to a hub according to the inventions.

As noted, both hubs 14, 24 are completely of the same color orange, but this need not be the case in other embodiments. A hub may be only partially orange in color or otherwise include orange marking(s) to serve as a matching feature to the matching feature of the syringes or other elements in an enteral safety system according to the inventions. In other words, a hub need not be an exact copy of the illustrated completely orange hub so long as the hub includes an indicator that may be observed as a matching feature to other elements of an enteral safety system.

Again referring to FIG. 1, hub 14 is connected to tubing 16 (also referred to herein as tube or enteral tubing). The tubing 16 (itself or with other elements such as an oral tip) may be referred to herein as an extension set. The tubing 16 is generally transparent in the exemplary embodiment, but for an orange stripe that runs the length of the tube. The orange stripe is relatively thin in this example (less than $\frac{1}{4}^{th}$ of the diameter of the tube), but may be of other widths. The stripe also may be made up or dashes or otherwise configured. The transparency of the tube 16 allows a user to view the contents while the orange stripe serves as an easy matching feature for connection of the extension set to the other elements of the system.

As noted, the exemplary tubing 16 uses orange striping as the matching feature, but other color(s), graphic(s) and/or text (including variations of the stripe) may be used instead so long as matching features among elements of a system have something in common. Further, the exemplary tubing 16 is generally transparent but for the stripe, but this does not have to be the case. Such alternative tubing may be only partially transparent (but for the matching feature) and/or otherwise allow for viewing of content of the tubing.

The tubing 16 connects to the exemplary side port element 18 that connects via oral tip 19 to hub 20. The side port element 18, the oral tip 19 and/or other elements as may be used with the exemplary embodiment may include the matching feature (in this case the particular color orange) so as to facilitate matching of the elements of the system 10. In the example of FIG. 1, the side port element 18 is shown as including an orange stripe similar to the orange stripe on the tubing 16, 22, but that does not need to be the case. A side port element without the orange stripe or other matching feature may be used with the exemplary embodiment.

The oral tip 19 and the hub 20 are completely the same color orange as used as the matching feature on the other elements of the system 10, but this need not be the case in other embodiments. An oral tip or hub may be only partially orange in color or otherwise include orange marking(s) to serve as a matching feature to the matching feature of the other elements in an enteral safety system according to the inventions. In other words, an oral tip or a hub need not be an exact copy of the illustrated completely orange oral tip and hub so long as the oral tip and hub include respectively an indicator that may be observed as a matching feature to other elements of an enteral safety system. The indicators may be the same or different between the oral tip 19 and the hub 20. The hub 20 also may be referred to herein as an enteral tubing-feeding tube hub at least to differentiate it from other types of hubs.

Referring again to FIG. 1, the hub 20 is connected to a feeding tube 21 (also referred to as tube or tubing). Tubing 21 is generally transparent in the exemplary embodiment, but for an orange stripe that runs the length of the tube. The orange stripe is relatively thin in this example (less than $\frac{1}{4}^{th}$ of the diameter of the tube), but may be of other widths. The stripe also may be made up or dashes or otherwise configured. The transparency of the tube allows a user to view the contents while the orange stripe serves as an easy matching feature for connection of the extension set to the other elements of the system. As noted, the exemplary tubing uses orange striping as the matching feature, but other color(s), graphic(s) and/or text (including variations of the stripe) may be used instead so long as matching features among elements of a system have something in common. Further, the exemplary tubing 21 is generally transparent but for the stripe, but this does not have to be the case. Such tubing may be only partially transparent (but for the matching feature) and/or otherwise allow for viewing of content of the tubing.

As noted, the exemplary embodiment includes a side port element 18. In addition to the extension set 16, side port element 18 connects another extension set including tubing 22 to the hub 20 for connection to the feeding tube 21. At the other end of tubing 22 (opposite to that end that is connected to the hub 20), the tubing 22 is connected via hub 24 to the syringe 26. The tubing 22 includes the orange stripe as described in connection with tubing 16. The other comments made regarding tubing 16 are also applicable to tubing 22. Hub 24 differs from hub 14 by having a tethered plug 27. The plug 27 may be used to cover the opening in the hub 24 when a syringe is connected to the hub 24. Advantageously, the plug 27 is attached to the body of the hub 24 so that the plug 27 is readily available for use.

The exemplary enteral safety system 10 illustrated in FIG. 1 has been described as including elements connected in a particular order, but the elements do not have to be connected in the order illustrated to conform to the inventions. The elements may be connected in an order as appropriate to the purpose. For example, it is not necessary in all cases for a syringe to be connected to an extension set before the syringe is connected to a feeding tube. Advantageously, the common matched feature among the elements of a system according to the inventions facilitates the easy and proper connection of the elements of the system.

In sum, the color orange was used as the matching feature among the elements of the exemplary enteral safety system 10 illustrated in FIG. 1. Thus, each element shown includes some "orange" color in some way so that a user may readily match the elements by such color. As noted, the orange color may be used as a matching feature in different ways in alternative embodiments. As also noted, other colors, graphics, and/or text may be used alternatively or in addition to the color orange as the matching feature and in various ways. For example, a matching feature need not necessarily be identical across all the elements that may constitute an enteral safety system so long as the elements each include something that is apparent to the user to constitute a "match" to the other elements of the system.

Even though the exemplary system elements (syringe, hub, extension set, feeding tube, etc.) have been described as being used in a system with each element having a common matching feature, the system elements may be used with elements and devices that do not include the matching feature. This non-matching use, however, may not assure the proper connectivity and ease of use in a system including such non-matching elements.

Figure 2:
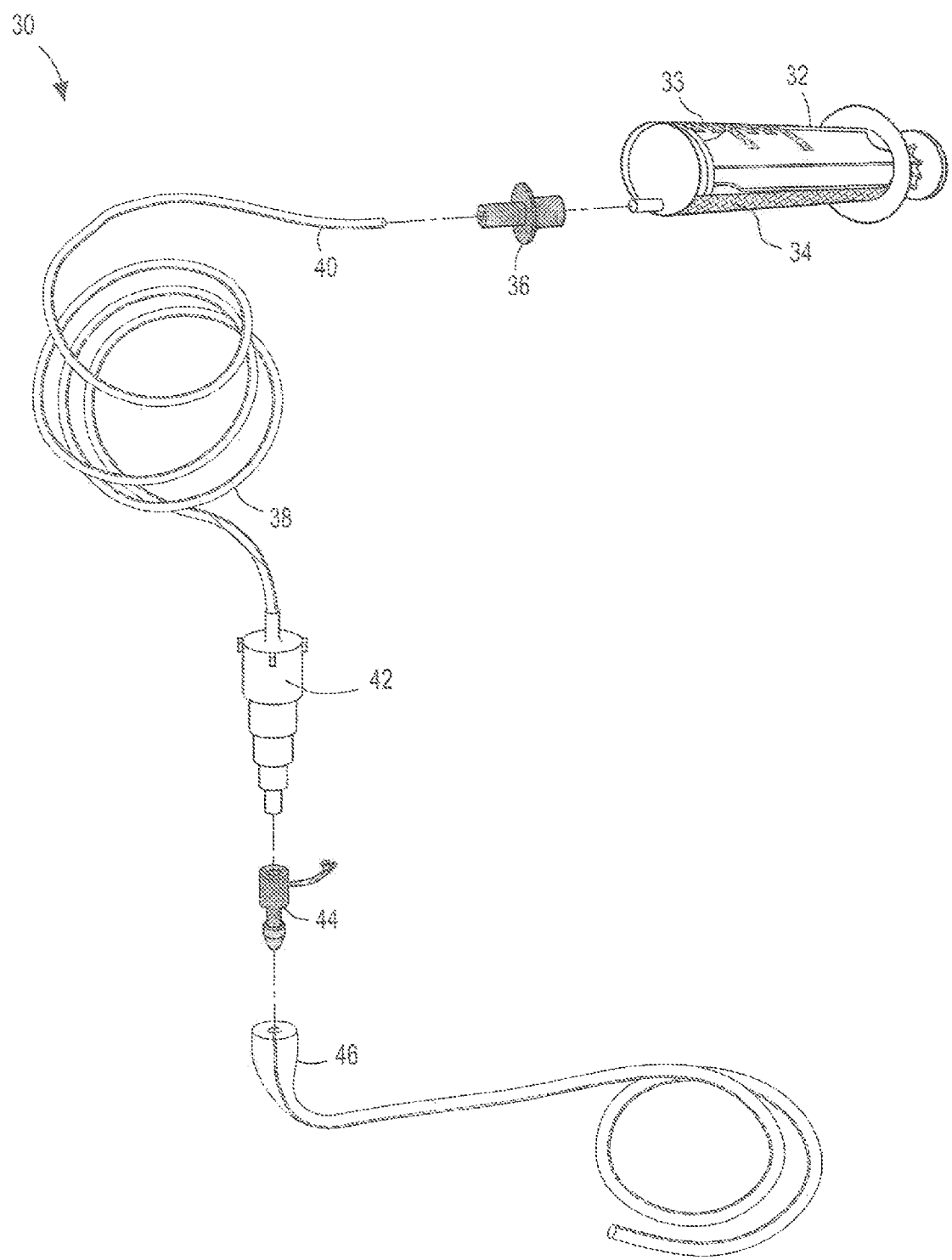
FIG. 2 shows another exemplary embodiment per the inventions.
Figure 3:
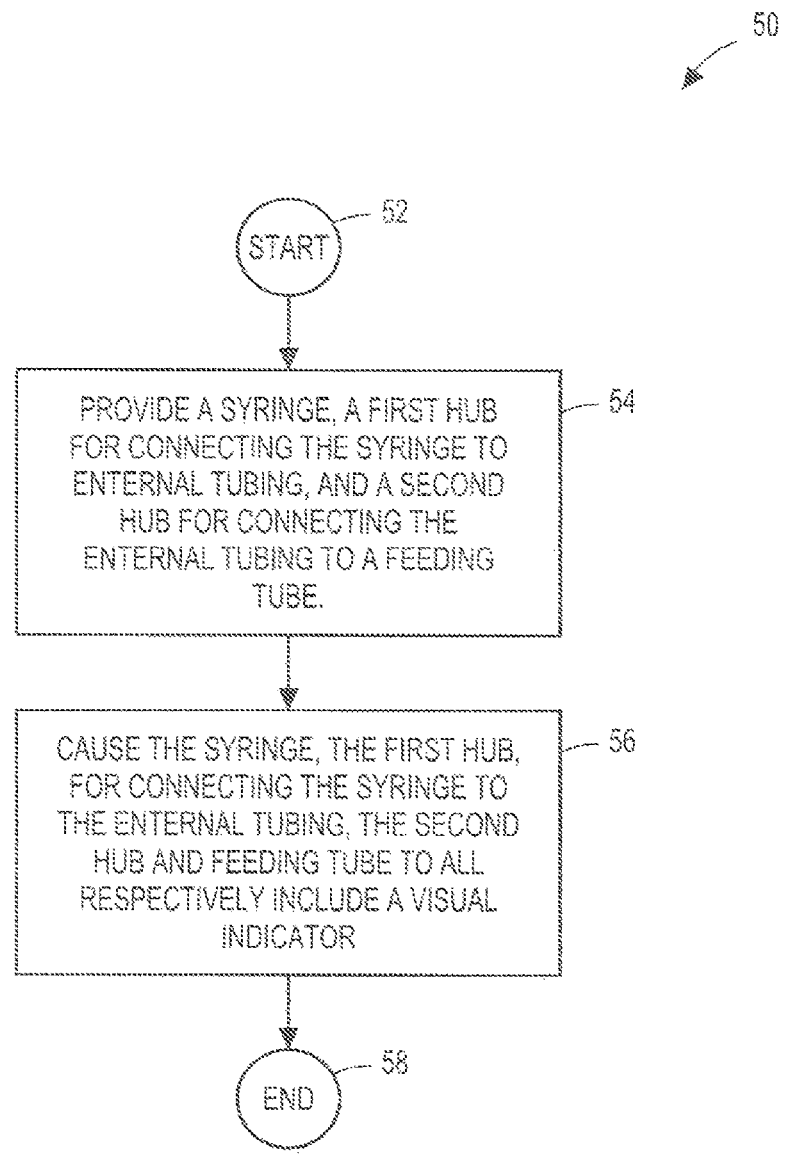
FIG. 3 shows an exemplary method per the inventions.

FIG. 2 shows another exemplary embodiment 30 according to the inventions. This enteral safety system 30 includes a syringe 32 with measurement marks 33. The syringe 32 includes a matching feature or visual indicator by having a lengthwise orange stripe 34. The syringe 32 connects to syringe-enteral tubing hub 36, which has the matching feature by being completely orange in color. The hub 36 connects to the extension set 38 including enteral tubing 40 and an oral tip 42. The extension set 38 includes the matching feature by the orange stripe on the enteral tubing 40. Note: the oral tip does not include the matching feature in this embodiment.

Still referring to the exemplary embodiment 30 shown in FIG. 2, the oral tip 42 connects the enteral tubing 40 to the enteral tubing-feeding tube hub 44. The hub 44 includes the matching feature by being completely orange in color. The hub 44 connects extension set 38 to the feeding tube 46. The tube 46 bears the matching feature by having a lengthwise orange stripe.

Another embodiment of the inventions includes an exemplary method for creating an enteral safety system 50. After start 52, in action 54 the method provides a syringe, a first hub for connecting the syringe to enteral tubing, and a second hub for connecting the enteral tubing to a feeding tube. In action 56, the method causes the syringe, the first hub, the enteral tubing, the second hub, and the feeding tube to all respectively include a visual indicator. The visual indicator may be a color and/or a graphic image. By this method 50, the enteral safety system is created by connecting the syringe, the first hub, the enteral tubing, the second hub, and the feeding tube by reference to each visual indicator.

CONCLUSION

The exemplary embodiments of the present inventions were chosen and described above in order to explain the principles of the invention and their practical applications so as to enable others skilled in the art to utilize the inventions including various embodiments and various modifications as are suited to the particular uses contemplated. The examples provided herein are not intended as limitations of the present invention. Other embodiments will suggest themselves to those skilled in the art. Therefore, the scope of the present invention is to be limited only by the claims below.

I claim:

1. An enteral safety system, comprising:
a syringe having a matching feature;
a syringe-enteral tubing hub for connecting the syringe to enteral tubing, the syringe-enteral tubing hub having the matching feature;
the enteral tubing having the matching feature;
the enteral tubing-feeding tube hub for connecting the enteral tubing to a feeding tube, the enteral tubing-feeding tube hub having the matching feature; and
the feeding tube having the matching feature.

2. The system of claim 1, wherein the matching feature comprises a color.

* * * * *